US008465739B2

(12) United States Patent
Kaisheva et al.

(10) Patent No.: US 8,465,739 B2
(45) Date of Patent: Jun. 18, 2013

(54) STABLE AQUEOUS PHARMACEUTICAL FORMULATIONS OF DACLIZUMAB ANTIBODIES

(75) Inventors: Elizabet A. Kaisheva, Belmont, CA (US); Supriya Gupta, Sunnyvale, CA (US); Shanti G. Duvur, Fremont, CA (US); Malathy Subramanian, Fremont, CA (US)

(73) Assignee: Abbvie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 13/226,372

(22) Filed: Sep. 6, 2011

(65) Prior Publication Data

US 2011/0318343 A1 Dec. 29, 2011

Related U.S. Application Data

(63) Continuation of application No. 12/954,512, filed on Nov. 24, 2010, now abandoned, which is a continuation of application No. 10/291,528, filed on Nov. 8, 2002, now abandoned.

(60) Provisional application No. 60/337,509, filed on Nov. 8, 2001.

(51) Int. Cl.
*A61K 39/395* (2006.01)

(52) U.S. Cl.
USPC .................. 424/130.1; 424/141.1; 424/144.1

(58) Field of Classification Search
None
See application file for complete search history.

(56) References Cited

U.S. PATENT DOCUMENTS

| 5,091,178 | A | 2/1992 | Hellstrom et al. |
| 5,744,132 | A | 4/1998 | Warne et al. |
| 6,165,467 | A | 12/2000 | Hagiwara et al. |
| 6,171,586 | B1 | 1/2001 | Lam et al. |
| 6,267,958 | B1 | 7/2001 | Andya et al. |
| 6,914,128 | B1 * | 7/2005 | Salfeld et al. ............. 530/387.3 |
| 2001/0014326 | A1 | 8/2001 | Andya et al. |

FOREIGN PATENT DOCUMENTS

| CA | 2365281 | | 8/2009 |
| WO | WO 89/11297 | A1 | 11/1989 |
| WO | WO 90/06764 | A1 | 6/1990 |
| WO | WO 90/11091 | A1 | 10/1990 |
| WO | WO 97/04801 | A1 | 2/1997 |
| WO | WO 97/45140 | A1 | 12/1997 |
| WO | WO 98/56418 | A1 | 12/1998 |
| WO | WO 98/22136 | A2 | 5/1999 |
| WO | WO 02/30463 | A2 | 4/2002 |
| WO | WO 02/096457 | A2 | 12/2002 |

OTHER PUBLICATIONS

Zenapax product sheet, 1997, p. 1-2.*
Advisory Action for U.S. Appl. No. 10/291,528, mailed Oct. 21, 2005.
Advisory Action for U.S. Appl. No. 10/291,528, mailed Feb. 6, 2007.
Advisory Action for U.S. Appl. No. 10/291,528, mailed Mar. 7, 2007.
Bio-world.com/buffers, pKa values and buffer ranges of important biological buffers, p. 1-5, 2005.
Board of Patent Appeals and Interferences Decision on Appeal in U.S. Appl. No. 10/291,528 (Appeal No. 2009-003947; Examiner affirmed) mailed Sep. 28, 2012.
Board of Patent Appeals and Interferences Decision on Rehearing in U.S. Appl. No. 10/291,528 (Request denied), mailed Dec. 13, 2010.
Bruner et al., 1997, "Size exclusion HPLC method for the determination of acidic fibroblast growth factor in viscous formulations," *J. Pharm. Bio. Anal.*, 15:1929-1935.
Examiner's answer to the Appeal Brief filed May 29, 2007, mailed Sep. 11, 2007.
Final Office Action for U.S. Appl. No. 10/291,528, mailed Jun. 13, 2005.
Final Office Action for U.S. Appl. No. 10/291,528, mailed Oct. 23, 2006.
Guss et al., 1993, Structure of the IgG-Binding regions of Streptococcal protein G, *EMBO J.*, 5(7):1567-1575.
Humira Product Information (approved by the FDA in Dec. 2002).
Jones, 1993, "Analysis of polypeptides and proteins," *A.Adv. Drug Delivery Rev.*, 10:29-90.
International Search Report for PCT/US2002/036093, mailed Aug. 5, 2003.
Lindmark et al., 1983, "Binding of Immunoglobulins to Protein A and Immunoglobulin Levels in Mammalian Sera," *J. Immunol. Meth.*, 62:1-13.
Mulligan et al., 1994, "Requirements for L-Selection in Neutrophil-Medicated Lung Injury in Rats," *J. Immunol.*, 151:832-840.
Non-Final Office Action for U.S. Appl. No. 10/291,528, mailed Jan. 12, 2005.
Non-Final Office Action for U.S. Appl. No. 10/291,528, mailed Apr. 27, 2006.
Non-Final Office Action for U.S. Appl. No. 12/954,512, mailed Mar. 7, 2011.
Pearlman et al., 1991, "Analysis of Protein Drugs," 247-301 in Peptide and Protein Drug Delivery, Vincent Lee Ed., Marcel Dekker, Inc., New York, N.Y. Pubs.
Remmele, Jr. et al., 1998, "Interleukin-1 Receptor (IL-1R) Liquid Formulation Development Using Differential Scanning Calorimetry," *Pharm. Res.*, 15(2):200.
Request for Rehearing of Board of Patent Appeals and Interferences Decision for U.S. Appl. No. 10/291,528, mailed Nov. 27, 2010.
Restriction Requirement for U.S. Appl. No. 10/291,528, mailed Oct. 21, 2004.

(Continued)

*Primary Examiner* — Yunsoo Kim
(74) *Attorney, Agent, or Firm* — Dechert LLP (57) ABSTRACT

This invention is directed to a stable liquid pharmaceutical formulation comprising a high concentration, e.g. 50 mg/ml or more, of antibody in about 20-60 mM succinate buffer or 30-70 mM histidine buffer, having pH from about pH 5.5 to about pH 6.5, about 0.01-0.1% polysorbate, and a tonicity modifier that contributes to the isotonicity of the formulation. This liquid formulation is stable at refrigerated temperature (2-8° C.) for at least 1 year, and preferably 2 years. This liquid formulation is suitable for subcutaneous injection. The preferred antibodies include Daclizumab, a humanized anti-IL-2 receptor monoclonal antibody; HAIL-12, a humanized anti-IL-12 monoclonal antibody; HuEP5C7, a humanized anti-L selectin monoclonal antibody; and Flintozumab, a humanized anti-gamma interferon monoclonal antibody.

9 Claims, 5 Drawing Sheets

OTHER PUBLICATIONS

Seekamp et al., 1994, "Role of Selectins in Local and Remote Tissue Injury Following Ischemia and Reperfusion," *Am. J Pathol.,* 11(3):592-598.

Shahrokh et al., 1994, "Approaches to Analysis of Aggregates and Demonstrating Mass Balance in Pharmaceuticals Protein (Basic Fibroblast Growth Factor) Formulations," *J. Pharm. Scien.,* 83(12):1645-1650.

Sluzy et al., 1994, "Chromatographic Methods for Quantitative Analysis of Native, Denatured and Aggregated Basic Fibroblast Growth Factor in Solution Formulations," *Pharm. Res.,* 11(4):485.

Supplementary European Search Report for EP Application No. 02802895.9, mailed Jun. 4, 2007.

Te Booy et al., 1982, "Evaluation of the Physical Stability of Freeze-Dried Sucrose-Containing Formulations by Differential Scanning Calorimetry," *Pharm. Res.,* 9(1):109.

Usami et al, 1986, "The Effect of pH, Hydrogen Peroxide and Temperature on the Stability of Human Monoclonal Antibody," *J. Pharm. Bio. Anal.,* 14:1133-1140.

\* cited by examiner

STABLE AQUEOUS PHARMACEUTICAL FORMULATIONS OF DACLIZUMAB ANTIBODIES

This application is a continuation of U.S. Ser. No. 12/954,512 filed Nov. 24, 2010, which is a continuation of U.S. Ser. No. 10/291,528 filed Nov. 8, 2002 (now abandoned), which is a nonprovisional and claims the benefit of U.S. Ser. No. 60/337,509 filed Nov. 8, 2001.

FIELD OF THE INVENTION

The present invention relates generally to the field of pharmaceutical formulation of antibodies. Specifically, the present invention relates to a stable, liquid, high concentration antibody formulation. This invention is exemplified by a stabilized liquid formulation of Daclizumab, an anti-IL2 receptor antibody; HAIL-12, a humanized anti-IL-12 monoclonal antibody; and HuEP5C7, a humanized anti-L selectin monoclonal antibody.

BACKGROUND OF THE INVENTION

Many protein preparations intended for human use require stabilizers to prevent denaturation, aggregation and other alternations to the proteins prior to the use of the preparation. This instability is manifested in the formation of soluble/insoluble particles, and is often increased when the protein preparation is stored over time and during shipping. A major aim in the development of protein drug formulations is to maintain both protein solubility, stability and bioactivity.

Immunoglobulins, in particular, are recognized as possessing characteristics that tend to form aggregates and particulates in solution, and as such, may require filtration before use for intravenous or subcutaneous injection. The formation of protein aggregates and particulates has long been a problem in the development of parenteral immunoglobulin products, especially when the immunoglobulins are formulated at high concentrations. Synagis™ (MedImmune) is a humanized monoclonal IgG1 antibody produced by recombinant DNA technology, directed to an epitope in the A antigenic site of the F protein of respiratory syncytial virus (RSV). Synagis™ is a composite of human (90%) and murine (10%) antibody sequences. Synagis™ is supplied as a sterile lyophilized product for reconstitution with sterile water for injection. Reconstituted Synagis™ is to be administered by intramuscular injection only. Upon reconstitution, Synagis™ contains the following excipients: 47 mM histidine, 3.0 mM glycine, 5.6% mannitol, and the active ingredient, IgG1 antibody, at a concentration of 100 milligrams per vial. The reconstituted Synagis™ is to be administered within 6 hours of reconstitution.

WO 89/11297 discloses a lyophilized monoclonal antibody formulation comprising a lyophilized formulation of 1-25 mg/ml IgG monoclonal antibody, 2-10% maltose, and sodium acetate, phosphate, or citrate buffer having a pH between 3.0 to 6.0.

WO 97/45140 discloses an aqueous preparation of anti-CD4 antibody concentrated to approximately 100 mg/ml in 100 mM sodium citrate, 0.05 mM EDTA, pH 6.0. The application discloses a slight rise in turbidity after concentration of the antibody, which likely reflects protein aggregation. Removing this aggregation requires addition of Polysorbate 80 and sterile filtration.

WO 90/11091 discloses injectable aqueous compositions comprising about 5 mg/ml of IgM, 2.5-5% (w/v) human serum albumin, in 8-20 mM phosphate buffer, 270 mM sodium chloride, pH 6.8-7.4.

U.S. Pat. No. 6,171,586 discloses a stable aqueous pharmaceutical formulation comprising a therapeutically effective amount of an antibody not subjected to prior lyophilization, an acetate buffer from about pH 4.8 to about 5.5, a surfactant, and a polyol, wherein the formulation lacks a tonicifying amount of sodium chloride.

U.S. Patent Application Publication No. US 2001/0014326A1 discloses a pre-lyophilized antibody formulation containing 25 mg/ml anti-IgE antibody, 5 mM histidine, pH 6.0, 85 mM sucrose, and 0.01% polysorbate 20.

U.S. Pat. No. 5,744,132 discloses a composition comprising 1-1000 μg/ml IL-12 antibody, 2% sucrose, 4.15% mannitol, 10 mM sodium succinate, and about 0.02% Tween® 20, having a pH of about 5.6.

U.S. Pat. No. 6,267,958 discloses a reconstituted formulation of 100 mg/ml rhuMab E25, in 20 mM histidine, pH 6.0, 340 mM sucrose, 0.04% polysorbate 20, and 0.9% benzyl alcohol.

U.S. Pat. No. 6,165,467 discloses a process for stabilizing a human monoclonal antibody composition produced by hybridoma cell line having accession number HB8307, which comprises dialyzing the human monoclonal antibody in a phosphate salt stabilized buffer solution having a pH from 7.2 to 7.4, said solution comprising 1-20 mg of D-mannitol per mg of said monoclonal antibody, 0.005-0.2 millimole of glycine per mg of said monoclonal antibody, and an amount of pH stabilizing phosphate salt to stabilize the pH of said solution.

There is a need for a stable liquid antibody preparation, wherein the antibody concentration is 50 mg/ml or greater; such preparation is suitable for parenteral administration, including intravenous, intramuscular, intraperitoneal, or subcutaneous injection to a human.

SUMMARY OF THE INVENTION

This invention is directed to a stable liquid pharmaceutical formulation comprising a high concentration, e.g., greater than 50 mg/ml, of an antibody in 20-60 mM succinate buffer or 30-70 mM histidine buffer (pH from about pH 5.5 to about pH 6.5), a tonicity modifier, and about 0.01-0.1% polysorbate. This formulation retains the physical, chemical, and biological stability of antibody and prevents the immunoglobulins intended for administration to human subjects from forming aggregates and particulates in the final product. Preferred antibodies of this invention include Daclizumab, a humanized anti-IL-2 receptor monoclonal antibody; HAIL-12, a humanized anti-IL-12 monoclonal antibody; and HuEP5C7, a humanized anti-L selectin monoclonal antibody; and Flintozumab, a humanized anti-gamma interferon monoclonal antibody.

The liquid antibody formulation is stable at refrigerated temperature (2-8° C.) for at least 1 year and preferably 2 years. This liquid formulation is also stable at room temperature (23-27° C.) for at least six months. This liquid formulation is suitable for subcutaneous injection.

DETAILED DESCRIPTION OF THE INVENTION

I. Definition

As used herein, the term "buffer" encompasses those agents which maintain the solution pH in an acceptable range and may include succinate (sodium), histidine, phosphate (sodium or potassium), Tris (tris (hydroxymethyl) aminomethane), diethanolamine, and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate phospate and other organic acid buffers.

"Pharmaceutically acceptable excipients" (vehicles, additives) are those inert substances that can reasonably be administered to a subject mammal and provide an effective dose of the active ingredient employed. These substances are added to a formulation to stabilize the physical, chemical and biological structure of the antibody. The term also refers to additives that may be needed to attain an isotonic formulation, suitable for the intended mode of administration.

The term "pharmaceutical formulation" refers to preparations which are in such form as to permit the biological activity of the active ingredients to be unequivocally effective, and which contain no additional components which are toxic to the subjects to which the formulation would be administered.

A "stable" formulation is one in which the protein therein essentially retains its physical stability, chemical stability, and biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, *A. Adv. Drug Delivery Rev.* 10:29-90 (1993). Stability can be measured at a selected temperature for a selected time period.

A "stable" liquid antibody formulation is a liquid antibody formulation with no significant changes observed at a refrigerated temperature (2-8° C.) for at least 12 months, preferably 2 years, and more preferably 3 years; or at room temperature (23-27° C.) for at least 3 months, preferably 6 months, and more preferably 1 year. The criteria for stability are as follows. No more than 10%, preferably 5%, of antibody monomer is degraded as measured by SEC-HPLC. The solution is colorless, or clear to slightly opalescent by visual analysis. The concentration, pH and osmolality of the formulation have no more than +/−10% change. Potency is within 70-130%, preferably 80-120% of the control. No more than 10%, preferably 5% of clipping (hydrolysis) is observed. No more than 10%, preferably 5% of aggregation is formed.

An antibody "retains its physical stability" in a pharmaceutical formulation if it shows no significant increase of aggregation, precipitation and/or denaturation upon visual examination of color and/or clarity, or as measured by UV light scattering, size exclusion chromatography (SEC-HPLC) and dynamic light scattering. In addition the protein conformation is not altered. The changes of protein conformation can be evaluated by fluorescence spectroscopy, which determines the protein tertiary structure, and by FTIR spectroscopy, which determines the protein secondary structure.

An antibody "retains its chemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical formulation, if the biological activity of the antibody at a given time is within a predetermined range of the biological activity exhibited at the time the pharmaceutical formulation was prepared. The biological activity of an antibody can be determined, for example, by an antigen binding ELISA assay.

The term "isotonic" means that the formulation of interest has essentially the same osmotic pressure as human blood. Isotonic formulations will generally have an osmotic pressure from about 270-328 mOsm. Slightly hypotonic osmotic pressure is 250-269 and slightly hypertonic osmotic pressure is 328-350 mOsm. Osmotic pressure can be measured, for example, using a vapor pressure or ice-freezing type osmometer.

"Tonicity modifiers" are those pharmaceutically acceptable inert substances that can be added to the formulation to provide an isotonity of the formulation. Tonicity modifiers suitable for this invention include salts and amino acids.

II. Analytical Methods

The following criteria are important in developing a stable pharmaceutical antibody formulation. The antibody formulation contains pharmaceutically acceptable excipients. The antibody formulation is formulated such that the antibody retains its physical, chemical and biological activity. The formulation is preferably stable for at least 1 year at refrigerated temperature (2-8° C.) and 6 months at room temperature (23-27° C.).

The analytical methods for evaluating the product stability include size exclusion chromatography (SEC-HPLC), dynamic light scattering test (DLS), differential scanning calorimetery (DSC), iso-asp quantification, potency, UV at 340 nm, and UV spectroscopy. SEC (*J. Pharm. Scien.*, 83:1645-1650, (1994); *Pharm. Res.*, 11:485 (1994); *J. Pharm. Bio. Anal.*, 15:1928 (1997); *J. Pharm. Bio. Anal.*, 14:1133-1140 (1986)) measures percent monomer in the product and gives information of the amount of soluble aggregates and clips. DSC (*Pharm. Res.*, 15:200 (1998); *Pharm. Res.*, 9:109 (1982)) gives information of protein denaturation temperature and glass transition temperature. DLS (*American Lab.*, November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration.

The iso-Asp content in the samples is measured using the Isoquant Isoaspartate Detection kit (Promega). The kit uses the enzyme Protein Isoaspartyl Methyltransferase (PIMT) to specifically detect the presence of isoaspartic acid residues in a target protein. PIMT catalyzes the transfer of a methyl group from S-adenosyl-L-methionine to isoaspartic acid at the a-carboxyl position, generating S-adenosyl-L-homocysteine (SAH) in the process. This is a relatively small molecule, and can usually be isolated and quantitated by reverse phase HPLC using the SAH HPLC standards provided in the kit.

The potency or bioactivity of an antibody can be measured by its ability to bind to its antigen. The specific binding of an antibody to its antigen can be quantitated by any method known to those skilled in the art, for example, an immunoassay, such as ELISA (enzyme-linked immunosorbant assay).

III. Preparation of Antibody

The invention herein relates to a stable aqueous formulation comprising an antibody. The antibody in the formulation is prepared using techniques available in the art for generating antibodies, exemplary methods of which are described in more detail in the following sections.

The antibody is directed against an antigen of interest. Preferably, the antigen is a biologically important polypeptide and administration of the antibody to a mammal may prevent or treat a disorder. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anticlotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3,-4,-5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β, including TGF-$β_1$, TGF-$β_2$, TGF-$β_3$, TGF-$β_4$, or TGF-$β_5$; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-12; receptors to interleukins IL-1 to IL-12; selectins such as L, E, and P-selectin; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

When using recombinant techniques, the antibody can be produced intracellularly, in the periplasmic space, or directly secreted into the medium. If the antibody is produced intracellularly, as a first step, the particulate debris, either host cells or lysed cells, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $Y_1$, $Y_2$, or $Y_4$ heavy chains (Lindmark et al., *J. Immunol. Meth.* 62:1-13 (1983)). Protein G is recommended for all mouse isotypes and for human $Y_3$ (Guss et al., *EMBO J.* 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSET™ chromatography on an anion or cation exchange resin (such as a polyaspartic acid column), chromatofocusing, SDS-PAGE, and ammonium sulfate precipitation are also available depending on the antibody to be recovered.

Preferred antibodies encompassed by the present invention include Daclizumab (USAN, United States Adopted Names), a humanized anti-IL-2 receptor antibody. Daclizumab is currently being marketed as Zenapax® for the prevention of organ rejection after renal transplantation and is administered through the intravenous route. Daclizumab is also useful for treating psoriasis, for which, the subcutaneous delivery is the preferred route of administration. For a subcutaneous delivery of antibody, high concentration of antibody is preferred. Daclizumab is a recombinant humanized monoclonal antibody, subclass IgG1. The molecule is composed of two identical heavy chain and two identical light chain subunits. Disulfide bridges link the four chains. Daclizumab monomer is approximately 150,000 daltons in molecular weight. Daclizumab binds to the p55 subunit of the IL-2 receptor expressed on activated T cells. The antigen target is designated CD25. Daclizumab is produced from a GS-NS0 cell line containing the heavy and light chain genes by fed-batch fermentation culture. Bioreactor harvests are processed to remove cells and debris and purified using a combination of ion-exchange and gel filtration chromatography and a series of ultrafiltration and filtration techniques to produce drug substance containing greater than 95% monomeric species.

Another preferred antibody is anti-interleukin 12 (IL-12) antibody. IL-12 is a cytokine synthesized by antigen presenting cells. It is composed of two subunits (p35 and p40), both must be present for functional activity. Functional IL-12 is also called IL-12p70. This cytokine preferentially acts on T helper cell type 1 (Th1) lymphocytes and natural killer cells by increasing their proliferative rate. One downstream effect is the secretion of interferon gamma (IFNg) by Th1 cells. Both of these functions (proliferative and IFNg production) can be easily assayed for and were used to detect IL-12 activity in samples. Certain antibodies to IL-12 have been shown to "neutralize" the above activities. Since Th1 cells have been implicated in playing a pivotal role in a variety of diseases, an antibody with neutralizing characteristics would have potential therapeutic value. 16G2 (Hoffman La Roche) is a murine antibody raised against IL-12p70. 16G2 has been shown to act in near stoichiometric amounts to IL-12 in a functional assay-the inhibition of proliferation of activated T cells from human peripheral blood (PBMC). This is an important characteristic because p40 dimers of IL-12 exist in serum and antibodies raised to the p40 subunit need to be used in excess amounts to neutralize the proliferative capacity of a given amount of IL-12. 16G2 was humanized at Protein Design Labs. (Fremont, Calif.) to give rise to HAIL-12 (humanized anti-IL-12, an IgG1 antibody).

Another preferred antibody is anti-L selectin antibody. Selectins, such as L, E, and P-selectin have been found to be associated with tissue damage during the course of ischemia and reperfusion. Neutrophils play an important role in this connection. It is assumed that selectin is required for the recruitment of neutrophils. L-selectin is important for the complete development of damage in skeletal muscle as well as in the lung (Seekamp, et al., *Am. J. Pathol.* 11:592-598 (1994). Mulligan, et al., *J. Immunol.* 151:832-840 (1994). HuEP5C7 (SMART Anti-L Selectin) is a humanized anti-L selectin monoclonal antibody, that contains mutant IgG2 Fc, cross reacts with both human E and P selectin antigens. It is currently being developed by Protein Design Labs, Inc. for various indications such as asthma, stroke, trauma, and certain autoimmune diseases.

Another preferred antibody is Flintozumab, an anti-gamma interferon antibody. Flintozumab is an IgG1 humanized monoclonal antibody developed by Protein Design Labs, Inc. for the treatment of immune disorders mediated by interferon-gamma (IFN-g), a proinflammatory cytokine. IFN-g induces the expression of major histocompatibility complex (MHC) class I and/or class II (HLA-DR) antigens, enhances the cytolytic activity of natural killer cells, activates macrophages, and modulates the immunoglobulin isotype profile of the humoral response. As a lymphokine, IFN-g also enhances the development of T helper cell type 1 (Th1), while suppressing the development of T helper cell type 2 (Th2) cells. Aberrations in the Th1/Th2 ratio have been implicated in a variety of autoimmune conditions.

IV. Preparation of the Formulation

After the antibody of interest is prepared as described above, a pharmaceutical formulation comprising the antibody is prepared. The formulation development approach is as follows: selecting the optimum solution pH, selecting buffer type and concentration, evaluating the effect of various excipients of the liquid stability, and optimizing the concentration of the screened excipients using an I-optimal experimental design (Statistics for Experimenters: An Introduction to Design, Data Analysis, and Model Building, Box, George E. P. et al., John Wiley and Sons, Inc., 1978).

The compositions of this invention minimize the formation of antibody aggregates and particulates and insure that the antibody maintains its bioactivity over time. The composition is a pharmaceutically acceptable liquid formulation containing a high concentration of an antibody in a buffer having a neutral or slightly acidic pH (pH 5.5-6.5), a surfactant, and a tonicity modifier.

The antibody in the composition is a high concentration of 50 mg/ml or greater, preferably 100 mg/ml or greater. A preferred composition of this invention contains Daclizumab, a humanized anti-IL2 receptor antibody; HAIL12, a humanized anti-IL-12 antibody; HaEP5C7, a humanized anti-L selectin antibody; and Flintozumab, a humanized anti-gamma interferon antibody.

A buffer of pH 5.5-6.5 is used in the composition. A buffer of pH 6.0-6.5 is preferred. Examples of buffers that control the pH in this range include succinate (such as sodium succinate), gluconate, histidine, citrate, phosphate, and other organic acid buffers. Succinate (pKa 5.63) is a preferred buffer for subcutaneous injection. Histidine (pK 5.97) is less preferred because of its susceptibility to oxidization, although such oxidation can be retarded by replacing the vial headspace with $N_2$ or adding an antioxidant. Citrate and phosphate buffers are much less preferred because it causes a painful reaction when injected subcutaneously. A preferred buffer contains about 20-60 mM sodium succinate. Another preferred buffer is 30-70 mM histidine buffer overlaid with $N_2$.

A surfactant is also added to the antibody formulation. Exemplary surfactants include nonionic surfactants such as polysorbates (e.g. polysorbates 20, 80, such as Tween® 20, Tween® 80) or poloxamers (e.g. poloxamer 188). The amount of surfactant added is such that it reduces aggregation of the formulated antibody and/or minimizes the formation of particulates in the formulation and/or reduces adsorption. The surfactant may be present in the formulation in an amount from about 0.005% to about 0.5%, preferably from about 0.01% to about 0.1%, more preferably from about 0.01% to about 0.05%, and most preferably from about 0.02% to about 0.04%.

A tonicity modifier, which contributes to the isotonicity of the formulations, is added to the present composition. The tonicity modifier useful for the present invention includes salts and amino acids. Salts that are pharmaceutically acceptable and suitable for this invention include sodium chloride, sodium succinate, sodium sulfate, potassuim chloride, magnesium chloride, magnesium sulfate, and calcium chloride. Preferred salts for this invention are NaCl and $MgCl_2$. $MgCl_2$ may also improve the antibody stability by protecting the protein from deamidation. A preferred concentration of NaCl is about 75-150 mM. A preferred concentration of $MgCl_2$ is about 1-100 mM. Amino acids that are pharmaceutically acceptable and suitable for this invention include proline, alanine, L-arginine, asparagine, L-aspartic acid, glycine, serine, lysine, and histidine. A preferred amino acid for this invention is proline. A preferred concentration of proline is than 200 mM.

EDTA, which is commonly used to stabilize a protein formulation, may also be included in the formulation. EDTA, as a chelating agent, may inhibit the metal-catalyzed oxidation of the sulfhydryl groups, thus reducing the formation of disulfide-linked aggregates. A preferred concentration of EDTA is 0.01-0.2%.

Exemplary liquid compositions are formulations comprising antibody at about 100 mg/ml or greater, about 20-60 mM sodium succinate (pH 6), about 0.01-0.1% polysorbate 20 or 80, and about 75-150 mM NaCl. This formulation retains the stability of biological activity of the monoclonal antibody, and prevents the immunoglobulins intended for administration to human subjects from physical, chemical and biological degradation in the final product.

The liquid antibody formulation of this invention is suitable for parenteral administration such as intravenous, intramuscular, intraperitoneal, or subcutaneous injection; particularly suitable for subcutaneous injection.

The invention is illustrated further by the following examples, which are not to be construed as limiting the invention in scope of the specific procedures described in them.

EXAMPLES

Example 1

Optimization of pH

To identify the optimum formulation for pH range and to identify major degradation pathways, a pH profile study was conducted. Sample formulations contained 5.0 mg/ml anti-IL2 receptor antibody (Daclizumab) in one of three buffers: 50 mM sodium acetate buffer at pH 4.0 or 5.0, 50 mM histidine at pH 5.5, 6.0, or 6.5, or 50 mM sodium phosphate buffer at pH 7.0 or 8.5. Independent formulations were incubated at either 5° C. or 45° C. with 100 RPM shaking for 4 weeks. The physical and chemical stability of each sample was assessed at 0 and 4 weeks by analytical methods including: pH and visual analysis, UV spectroscopy at 340 nm, size exclusion chromatography (SEC-HPLC), fluorescence spectroscopy, dynamic light scattering (DLS), differential scanning calorimetry (DSC), Promega IsoQuant Assay, capillary isoelectric focusing (cIEF), SDS-PAGE (reduced and non-reduced), and bioactivity assessments (ELISA).

Figure 1A:
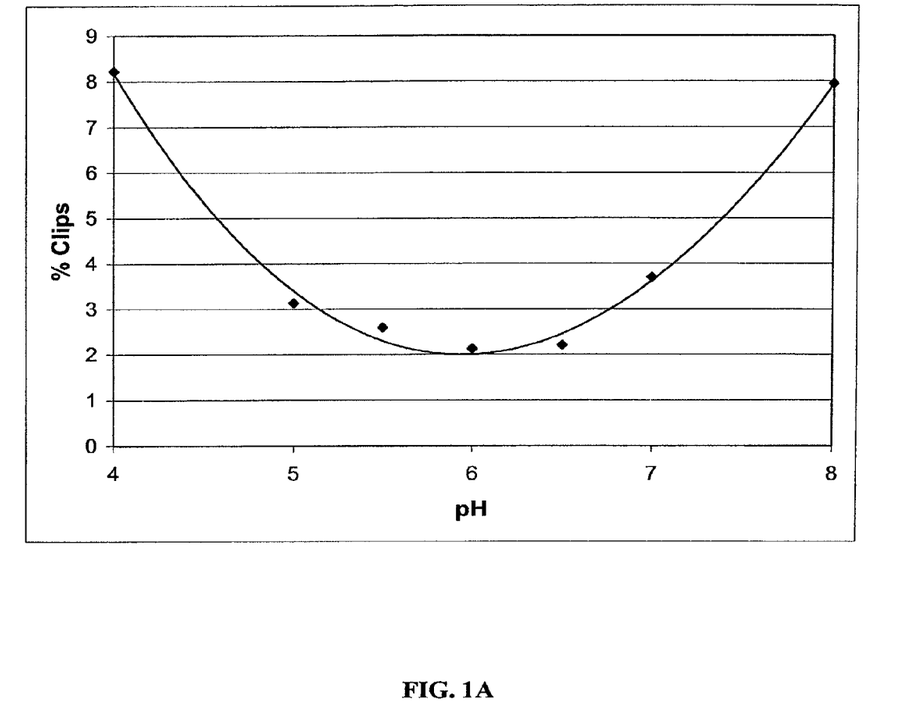
FIG. 1A shows the percent clips formation.
Figure 1B:
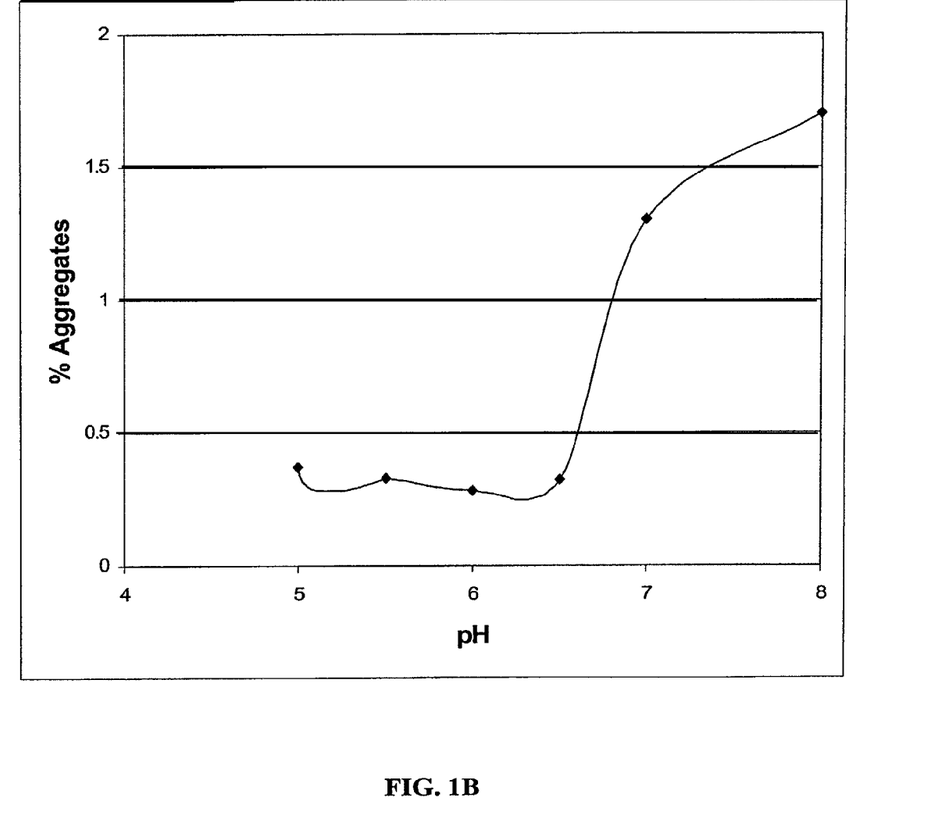
FIG. 1B shows the percent aggregates, at various pH levels following a four-week incubation of the sample at 45° C., as assessed by SEC-HPLC.

SEC-HPLC performed on samples after four weeks of incubation at 45° C. showed that clipping is a major degradation pathway for the liquid formulation, as shown in FIG. 1A by the percent of clips recovered at various pH levels with SEC. Both the percent of clips and the percent of aggregates (FIG. 1B) determined by SEC were reduced at the midrange pH values of 5.5 to 6.5.

Figure 2:
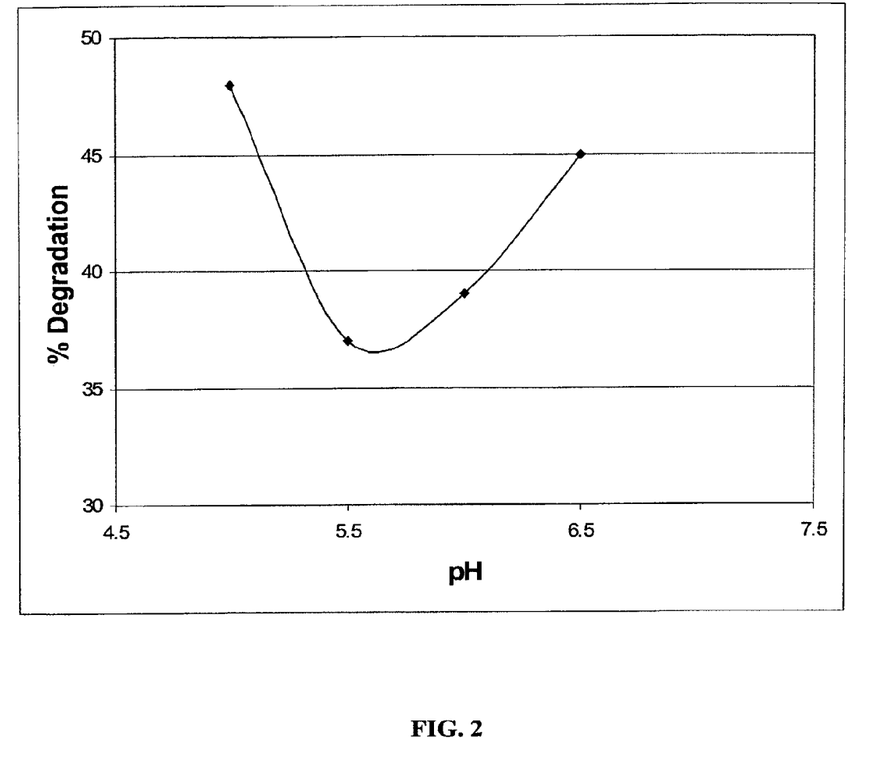
FIG. 2 shows the percent of degradation obtained at various pH levels as assessed by cIEF following a four-week incubation of the sample at 45° C.

FIG. 2 shows the percent of degradation obtained at various pH levels as assessed by cIEF following a four-week incubation of the sample at 45° C. Minimal degradation was obtained at a pH value of about 5.5.

Figure 3:
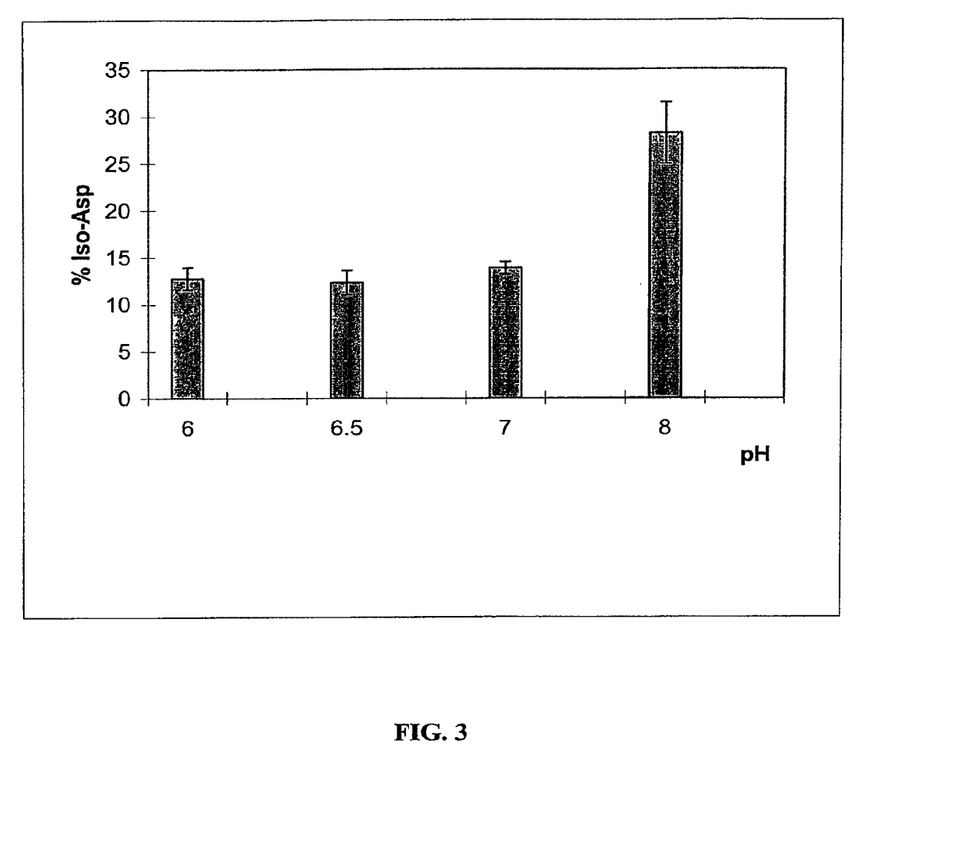
FIG. 3 shows the percent of iso-aspartic acid formed at various pH levels as assessed by the Promega IsoQuant kit following a four-week incubation of the sample at 45° C.

FIG. 3 shows the percent of iso-aspartic acid formed at various pH levels as assessed by the Promega IsoQuant kit following a four-week incubation of the sample at 45° C. Iso-aspartic acid formation (deamidation) was minimized at pH values of 6 and 6.5, and increased sharply at pH 8.0.

The results from this experiment indicate that pH 5.5 to 6.5 and preferable pH 6.0 to 6.5, are the optimal pH which minimize antibody degradation and aggregation.

Example 2

Optimization of Buffers

In this experiment, independent formulations contained 5.0 mg/ml Daclizumab antibody in 50 mM sodium succinate, pH 6.0; and 50 mM histidine, pH 6.0, with and without $N_2$ gassing. Sodium citrate buffer was not included because of reports of pain on subcutaneous injection. The bioactivity (potency) at time 0, and after 4, 8, and 12 weeks of incubation at 37° C. was measured by ELISA using microplates coated with recombinant human IL2 alpha receptor (IL-2 sRα) antigen, and goat anti-human IgG-HRP conjugate.

Figure 4:
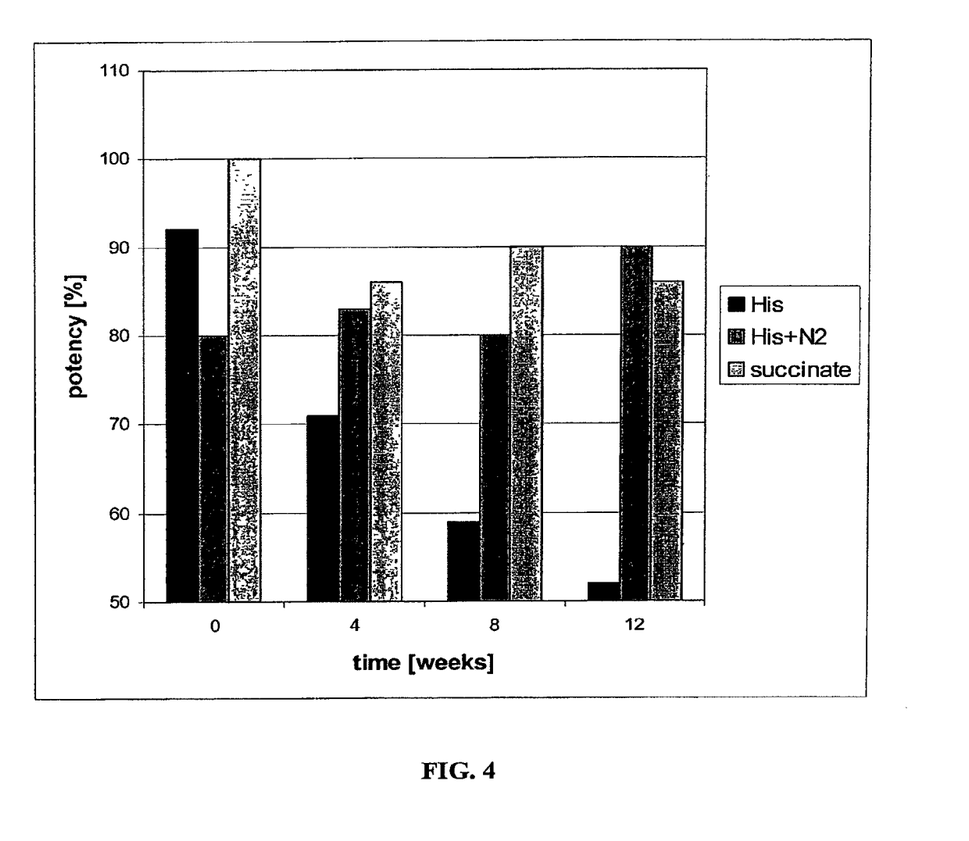
FIG. 4 shows the effect of different buffers over time on potency following incubation at 37° C.

FIG. 4 shows the effect of different buffers over time on potency following incubation at 37° C. Highest stability of the antibody formulation was achieved through 8 weeks with 50 mM sodium succinate buffer at pH 6.0. Formulations in histidine alone rapidly (less than 8 weeks) lost their potency as the buffer oxidized. Potency of the formulation remained greater than 80% for at least 12 weeks in either sodium succinate buffer or histidine buffer gassed with $N_2$ to prevent oxidation.

Example 3

Screening of Excipients

Objectives

This study was conducted to screen various excipients for the formulation of Daclizumab antibody at 50 mg/mL. From the pH optimization study conducted earlier (Example 1), the formulation stability was maximized in the pH range of 6.0-6.5. Therefore in this study, excipients were screened in two buffers; 50 mM phosphate, pH 6.5 and 50 mM succinate, pH 6.0. The stability of antibody was monitored in the two buffers for 3 weeks at 5° C. and 45° C. with shaking at 100 RPM at a concentration of 50 mg/mL. The excipients examined included: surfactants (Tween 80® and Tween 20®), salts (NaCl and $MgCl_2$), antioxidants (EDTA and methionine), amino acids (glycine, lysine, serine and proline), and co-solvents (glycerol and ethanol). Various analytical techniques (clarity, pH, SEC-HPLC, UV-Vis, and cIEF) were used to characterize the excipient-containing formulations.

Sample Preparation

The Daclizumab antibody was in a 67 mM sodium phosphate formulation (without Tween® 80) at a concentration of 6.6 mg/mL. This material was concentrated to about 30 mg/mL in the Pellicon II (Millipore) unit, and subsequently, buffer exchanged into two selected buffers (50 mM sodium phosphate pH 6.5, and 50 mM sodium succinate pH 6.0) using the 50 mL amicon stir cell (Millipore). During the third and final buffer exchange step, the material was also concentrated to a final concentration of ~125 mg/mL. Finally, the antibody was filtered through 0.8 μm membrane (Uniflo). The post filtration protein concentration was determined to be approximately 100 mg/mL for the phosphate buffer sample and 97 mg/mL for the succinate buffer sample.

The target concentration of the excipients at which they were screened is shown in Table 1. The formulations were prepared by either weighing the required amount of the excipients directly into the vial (e.g. all amino acids) or by preparing concentrated stock solutions of the excipients. The excipients were added to 0.5 mL of the appropriate buffer solution and the pH adjusted to the desired value with either 1N HCl or 10% NaOH. Subsequently, 0.5 mL of the concentrated antibody solution in the appropriate buffer (~100 mg/mL) was added to attain the target concentration of 50 mg/mL. This procedure was adopted to prevent protein degradation due to direct contact with concentrated excipients. The 1 mL solution was split into two vials with 0.5 mL fill each. One vial was used for initial T=0 analysis and then stored at 2-8° C. for the 3 week time point analysis at 2-8° C. The other vial was incubated at 45° C. with shaking at 100 RPM for 3 weeks and analyzed at the end of that time period.

TABLE 1

List of excipients and their concentrations as used in the study.

| # | Excipient | Target Conc. |
|---|---|---|
| 1 | Tween 80 | 0.05% |
| 2 | EDTA | 0.05% |
| 3 | NaCl | 150 mM |
| 4 | Methionine | 100 mM |
| 5 | Glycine | 200 mM |
| 6 | Serine | 200 mM |
| 7 | Proline | 200 mM |
| 8 | Lysine | 200 mM |
| 9 | $MgCl_2$ | 100 mM |
| 10 | Tween 20 | 0.05% |
| 11 | Glycerol | 5.0% |
| 12 | Ethanol | 5.0% |

Analytical Methods

At each of the two time points, the samples were analyzed using various analytical techniques. Solution clarity was visually examined by holding the sample vials up against a black background under fluorescent lighting. The solution was inspected for insoluble species and color changes were recorded. Size exclusion chromatography was performed using a Perkin Elmer HPLC unit with diode array detection and two Tosohaas columns connected in series. The samples were diluted approximately 5 fold with the corresponding buffer to bring the concentration to about 1 mg/mL and 100 μL of the sample was injected onto the column. The sample concentration was measured by UV spectroscopy using the Perkin Elmer Lambda Bio 40 spectrophotometer.

The samples from the 3-week time point were analyzed by Capillary Isoelectric Focusing on the BioRAD CE (BioFocus 3000) System. All the samples were diluted to 0.25 mg/mL with water and a 1:1 dilution (to a final concentration of 0.125 mg/mL) was made with the pharmalyte solution containing TEMED and two internal pI markers, 8.4 and 10.1. The capillary used was an eCAP with neutral coating (Beckmann, 56 cm length, 50 um ID).

The potency of samples formulated in the succinate buffer with the excipients, Tween-80, EDTA, NaCl and $MgCl_2$ was tested after 3 weeks of incubation at 5 and 45° C. It was a bio-assay involving KIT-225-K6 cells.

Results

There were 24 samples at time point T=0 as 12 different excipients were monitored in two different buffers. At the 3 week time point, there were 48 samples to be analyzed (12 different excipients×2 temperatures×2 buffers=48). Assays performed include concentration determination by UV-Vis, pH, Clarity, SEC-HPLC, and CIEF.

(a) Sample Clarity

Sample appearance is indicated in Table 2. All samples were clear in both the buffers at the initial time point T=0. At the 3 week time point, all samples in the phosphate buffer except the one containing lysine were clear at 5° C. In the same buffer, at 45° C., the samples containing amino acids (glycine, serine, proline and lysine) appeared clear but had some thread like floaties in the vials. The sample with $MgCl_2$ had clear crystals settled in the bottom of the vial.

In the succinate buffer, all samples except the amino acid containing formulations were clear after three weeks of incubation at 5° C. The samples with proline and lysine were the most turbid. At 45° C., all samples in succinate buffer were clear at the 3 week time point.

TABLE 2

Sample clarity determined by fluorescence light at T = 0 and T = 4 weeks at 5 and 45° C. in the Na-succinate (pH 6.0) and Na-phosphate (pH 6.5) buffers.

| Sample | Phosphate T = 0 Clarity | Phosphate T = 3 wks Clarity, 5° C. | Phosphate T = 3 wks Clarity, 45° C. | Succinate T = 0 Clarity | Succinate T = 3 wks Clarity, 5° C. | Succinate T = 3 wks Clarity, 45° C. |
|---|---|---|---|---|---|---|
| Tween-80 | Clear | Clear | Clear | Clear | Clear | Clear |
| EDTA | Clear | Clear | Clear | Clear | Clear | Clear |
| NaCl | Clear | Clear | Clear | Clear | Clear | Clear |
| Methionine | Clear | Clear | Clear | Clear | Turbid | Clear |
| Glycine | Clear | Clear | Clear | Clear | Turbid | Clear |
| Serine | Clear | Clear | Clear | Clear | Turbid | Clear |
| Proline | Clear | Clear | Clear | Clear | Turbid | Clear |
| Lysine | Clear | Turbid | Clear | Clear | Turbid | Clear |
| $MgCl_2$ | Clear | Clear | Clear | Clear | Clear | Clear |
| Tween-20 | Clear | Clear | Clear | Clear | Clear | Clear |
| Glycerol | Clear | Clear | Clear | Clear | Clear | Clear |
| Ethanol | Clear | Clear | Clear | Clear | Clear | Clear |

(b) SEC-HPLC

Results of SEC-HPLC are tabulated in Table 3(A-C). Table 3A indicates the % monomer for all samples being investigated in this study. The % monomer at T=0 for all samples was ≧99%. At the three weeks time point, no significant change was observed in the % monomer for the 5° C. samples in both buffers. However, at 45° C., all samples indicated a slight drop in the % monomer (<5%). For samples formulated in the phosphate buffer, the % monomer varied from 94.08 (methionine) to 97.29 (proline), while for the samples formulated in the succinate buffer, the % monomer varied from 95.86 (methionine) to 97.55 (Tween-80). In both the buffers, the methionine and glycine containing formulations showed the most significant drop in % monomer. The decrease in % monomer was mostly due to clip formation.

Table 3B lists the % aggregate formation in all samples being investigated in this study. It is clear from these results that the increase in aggregate formation during the 3-week duration is minimal for all samples at 5° C. in both buffers. After 3 weeks of incubation at 45° C., samples in the phosphate buffer showed an increase in % aggregate ranging from 0.40% (EDTA) to 2.40% (glycine). In the succinate buffer, the aggregate formation was slightly lower; ranging from 0.7% (methionine) to 1.09% (glycine) after the 3 week incubation period. One of the hypotheses that supports these results is that if aggregate formation is due to oxidation, it may be slowed down in the succinate buffer due to the metal chelating properties of the succinate buffer.

Table 3C lists the % clip formation in all samples being investigated in this study. At the initial time point, the % clipping ranged from ~0.2-0.4% in all samples. For all samples incubated at 5° C., the % increase in clips was insignificant over the 3-week period. At 45° C., a significant increase in the rate of clip formation was observed. For samples formulated in the phosphate buffer, the % clipping varied from 4.74 (methionine) to 1.5% (proline, glycerol and ethanol), while in the succinate buffer, the range was 1.48% (Tween-80) to 3.44 (methionine). In general, an increase in the clip formation was observed in the amino acid containing formulations. Further, the rate of clip formation appears to be higher in the phosphate buffer. This may be attributed to the pH difference of the Na-succinate and Na-phosphate buffers (pH 6.0 and 6.5, respectively), indicating base catalyzed hydrolysis as being the primary reason for clip formation

TABLE 3A

% Monomer as determined by SEC at T = 0 and 3 weeks at 5° C. and 45° C. in the Na-succinate (pH 6.0) and Na-phosphate (pH 6.5) buffers.

| Sample | Phosphate T = 0 % Mono | Phosphate T = 3 wks % Mono, 5° C. | Phosphate T = 3 wks % Mono, 45° C. | Succinate T = 0 % Mono | Succinate T = 3 wks % Mono, 5° C. | Succinate T = 3 wks % Mono, 45° C. |
|---|---|---|---|---|---|---|
| Tween-80 | 99.36 | 99.48 | 96.71 | 99.43 | 99.51 | 97.55 |
| EDTA | 99.37 | 99.42 | 96.43 | 99.42 | 99.53 | 97.51 |
| NaCl | 99.37 | 99.41 | 96.84 | 99.42 | 99.53 | 97.31 |
| Methionine | 99.42 | 99.42 | 94.08 | 99.47 | 99.53 | 95.86 |
| Glycine | 99.41 | 99.42 | 95.90 | 99.46 | 99.53 | 96.46 |
| Serine | 99.41 | 99.45 | 96.15 | 99.45 | 99.53 | 97.29 |
| Proline | 99.40 | 99.43 | 97.29 | 99.45 | 99.52 | 97.06 |
| Lysine | 99.34 | 99.62 | 95.45 | 99.45 | 99.57 | 96.28 |
| MgCl$_2$ | 99.37 | 99.44 | 97.12 | 99.47 | 99.53 | 96.62 |
| Tween-20 | 99.17 | 99.53 | 96.33 | 99.44 | 99.53 | 97.27 |
| Glycerol | 99.41 | 99.59 | 96.32 | 99.43 | 99.48 | 97.46 |
| Ethanol | 99.41 | 99.42 | 97.24 | 99.31 | 99.19 | 97.42 |

TABLE 3B

% Aggregate as determined by SEC at T = 0 and 3 weeks at 5° C. and 45° C. in the Na-succinate (pH 6.0) and Na-phosphate (pH 6.5) buffers.

| Sample | Phosphate T = 0 % Agg | Phosphate T = 3 wks % Agg, 5° C. | Phosphate T = 3 wks % Agg, 45° C. | Succinate T = 0 % Agg | Succinate T = 3 wks % Agg, 5° C. | Succinate T = 3 wks % Agg, 45° C. |
|---|---|---|---|---|---|---|
| Tween-80 | 0.41 | 0.00 | 1.61 | 0.36 | 0.36 | 0.96 |
| EDTA | 0.39 | 0.43 | 0.40 | 0.35 | 0.35 | 0.96 |
| NaCl | 0.40 | 0.43 | 1.23 | 0.33 | 0.34 | 0.85 |
| Methionine | 0.36 | 0.41 | 1.18 | 0.32 | 0.34 | 0.70 |
| Glycine | 0.38 | 0.42 | 2.40 | 0.33 | 0.35 | 1.09 |
| Serine | 0.38 | 0.40 | 2.15 | 0.32 | 0.33 | 0.91 |
| Proline | 0.38 | 0.41 | 1.14 | 0.35 | 0.34 | 0.86 |
| Lysine | 0.39 | 0.36 | 1.50 | 0.32 | 0.30 | 0.64 |
| MgCl$_2$ | 0.38 | 0.42 | 0.60 | 0.32 | 0.34 | 0.82 |
| Tween-20 | 0.40 | 0.44 | 1.55 | 0.34 | 0.34 | 1.00 |
| Glycerol | 0.37 | 0.40 | 2.13 | 0.35 | 0.32 | 0.94 |
| Ethanol | 0.37 | 0.43 | 1.26 | 0.28 | 0.38 | 0.91 |

TABLE 3C

% Clipping as determined by SEC at T = 0 and 3 weeks at 5° C. and 45° C. in the Na-succinate (pH 6.0) and Na-phosphate (pH 6.5) buffers.

| Sample | Phosphate T = 0 % Clip | Phosphate T = 3 wks % Clip, 5° C. | Phosphate T = 3 wks % Clip, 45° C. | Succinate T = 0 % Clip | Succinate T = 3 wks % Clip, 5° C. | Succinate T = 3 wks % Clip, 45° C. |
|---|---|---|---|---|---|---|
| Tween-80 | 0.21 | 0.52 | 1.67 | 0.22 | 0.11 | 1.48 |
| EDTA | 0.22 | 0.15 | 2.00 | 0.22 | 0.12 | 1.53 |
| NaCl | 0.24 | 0.16 | 1.93 | 0.21 | 0.12 | 1.85 |
| Methionine | 0.21 | 0.16 | 4.74 | 0.21 | 0.13 | 3.44 |
| Glycine | 0.20 | 0.15 | 1.70 | 0.21 | 0.12 | 2.41 |
| Serine | 0.21 | 0.14 | 1.69 | 0.23 | 0.12 | 1.81 |

TABLE 3C-continued

% Clipping as determined by SEC at T = 0 and 3 weeks at 5° C. and 45° C. in the Na-succinate (pH 6.0) and Na-phosphate (pH 6.5) buffers.

| Sample | Phosphate T = 0 % Clip | Phosphate T = 3 wks % Clip, 5° C. | Phosphate T = 3 wks % Clip, 45° C. | Succinate T = 0 % Clip | Succinate T = 3 wks % Clip, 5° C. | Succinate T = 3 wks % Clip, 45° C. |
|---|---|---|---|---|---|---|
| Proline | 0.22 | 0.16 | 1.58 | 0.21 | 0.13 | 2.08 |
| Lysine | 0.24 | 0.02 | 3.05 | 0.23 | 0.12 | 3.09 |
| MgCl$_2$ | 0.21 | 0.14 | 2.28 | 0.21 | 0.13 | 2.55 |
| Tween-20 | 0.44 | 0.03 | 2.12 | 0.22 | 0.11 | 1.73 |
| Glycerol | 0.23 | 0.01 | 1.54 | 0.22 | 0.20 | 1.61 |
| Ethanol | 0.22 | 0.14 | 1.51 | 0.41 | 0.40 | 1.67 |

(c) Capillary Electrophoresis

All the samples from this study were analyzed by capillary electrophoresis (cIEF) on the BioRAD system. A typical cIEF profile of Daclizumab shows four peaks. Typically on accelerated aging at high temperatures, the area of the main isoform peak decreases followed by an increase in the other isoform peaks, which indicates the conversion of one isoform to another isoform. The % degradation is calculated by percent decrease in the peak area of the main isoform:

% Degradation=[Peak Area at $T$=0−Peak Area at 45° C.]×100% [Peak Area at $T$=0]

Our results indicate that the 45° C. samples are more degraded in the phosphate buffer (pH 6.5) when compared with similar samples in the succinate buffer (pH 6.0). The best electropherograms were seen for the excipients, EDTA, NaCl, lysine and MgCl$_2$. The % degradation after 3 weeks for the 5° C. versus the 45° C. could not be calculated for the samples containing Tween 80, Tween 20, serine and proline as their electropherograms were very collapsed and the peaks indistinguishable.

(d) Potency

Based on the results of this study, the Na-succinate buffer appears to be more promising than the Na-phosphate buffer. Thus, potency assessments were done for the most stabilizing excipients in the Na-succinate buffer only. This included the formulations containing Tween-80, EDTA, NaCl and MgCl$_2$, subject to three weeks of incubation at 5 and 45° C. Results (Table 4) showed that the potency of all formulations was within specifications, indicating that the underlying chemical and physical degradation processes are not significantly altering the protein activity.

TABLE 4

Potency results of selected formulations in succinate buffer at T = 3 weeks at 5 and 45° C.

| Sample | pH | % Potency |
|---|---|---|
| Tween-80, 5° C. | 6.0 | 105 |
| Tween-80, 45° C. | 6.0 | 80 |
| EDTA, 5° C. | 6.0 | 103 |
| EDTA, 45° C. | 6.0 | 74 |
| NaCl, 5° C. | 6.0 | 105 |
| NaCl, 45° C. | 6.0 | 98 |
| MgCl$_2$, 5° C. | 6.0 | 112 |
| MgCl$_2$, 45° C. | 6.0 | 96 |

Discussion

Based on the results of this study, the stability of formulation was higher in the Na-succinate buffer at pH 6.0, compared with the Na-phosphate buffer at pH 6.5. This is primarily due to base-catalyzed hydrolysis that is accelerated at the higher pH of 6.5, causing an increase in the rate of clip formation. Thus, the Na-succinate buffer at pH 6.0 is the selected buffer for all future studies. Results of this study also clearly indicated that in both buffers, the amino acids (glycine, lysine, serine, proline, and methionine) did not have a stabilizing effect on the protein stability. As shown by the data on sample clarity, all amino acid containing formulations indicated the formation of insoluble aggregates at 45° C.

The excipient MgCl$_2$ was selected in this study based on the hypothesis that it might protect the protein against dimidiation. While MgCl$_2$ precipitated in the Na-phosphate buffer; in the Na-succinate buffer, based on the cIEF data, MgCl$_2$ has a stabilizing effect on the protein. Ethanol was also included as an excipient to test if it stabilized the protein against deamidation by lowering the dielectric constant of the solution. The results, however, do not support this hypothesis. Finally, Tween-80, EDTA, and NaCl, the excipients most commonly used to stabilize protein formulations, did not show any destabilizing effect on the protein in either buffer.

Further experiments were conducted in the Na-succinate buffer at pH 6.0; the effect of the excipients (MgCl$_2$, Tween-80, NaCl, and EDTA) was further examined on the protein stability. The results indicate that to formulate an antibody at 100 mg/mL with 100 mM NaCl, the optimal concentration of Tween 80 falls in the range of 0.02-0.03%. Results also indicate that increasing the salt concentration (100-150 mM) could further stabilize the formulation. Thus, the concentration of NaCl should be maximized while maintaining the tonicity requirements. The results also indicate that the stability of the Tween 80 and NaCl containing formulation could be enhanced by adding EDTA in the concentration range of 0.35-0.5%. The addition of MgCl$_2$ in the concentration range of 0-50 mM also could have a favorable effect. The results also indicate that the excipient concentrations for the most stable formulation are: 150 mM NaCl, 0.05% Tween 80, 0.03-0.04% EDTA and 60-70 mM MgCl$_2$, however, these conditions are not practical because they do not provide isotonic conditions.

Example 4

Stability Data of Two Daclizumab Antibody Formulations in Succinate Buffer

Formulations 1 and 2 were prepared according to Example 3.

Formulation 1: 100 mg/ml Daclizumab antibody, 30 mM sodium succinate (pH 6.0) 100 mM NaCl and 0.03% Tween®-80.

Formulation 2: same as Formulation 1, plus 0.05% EDTA.

The stability results of Formulations 1 and 2 at T=0, 2 weeks, 4 weeks, 8 weeks, and 12 weeks are shown as follows at 5, 25, and 37° C. (Table 5).

TABLE 5

Stability results of Formulations 1 and 2.

| Sample | Clarity | % Monomer | % Clip | % Aggregate | % Potency |
|---|---|---|---|---|---|
| T = 0 | | | | | |
| F1 | Clear | 98.27 | 0.77 | 0.96 | 100 |
| F2 | Clear | 98.27 | 0.77 | 0.96 | 90 |
| T = 2 Weeks | | | | | |
| F1-5 C. | Clear | 98.31 | 0.73 | 0.95 | NA |
| F1-25 C. | Clear | 98.03 | 0.82 | 1.14 | NA |
| F1-37 C. | Clear | 97.11 | 1.21 | 1.69 | NA |
| F2-5 C. | Clear | 98.20 | 0.92 | 0.90 | NA |
| F2-25 C. | Clear | 97.90 | 1.09 | 1.06 | NA |
| T = 4 Weeks | | | | | |
| F1-5 C. | Clear | 98.30 | 0.74 | 0.96 | 93 |
| F1-25 C. | Clear | 97.80 | 0.92 | 1.28 | 88 |
| F1-37 C. | Clear | 96.20 | 1.77 | 2.03 | 84 |
| F2-5 C. | Clear | 98.30 | 0.77 | 0.93 | 94 |
| F2-25 C. | Clear | 97.85 | 0.95 | 1.20 | 92 |
| F2-37 C. | Clear | 96.30 | 1.83 | 1.87 | 80 |
| T = 8 Weeks | | | | | |
| F1-5 C. | Clear | 98.24 | 0.73 | 0.95 | 96 |
| F1-25 C. | Clear | 97.51 | 0.82 | 1.14 | 96 |
| F1-37 C. | Clear | 94.76 | 1.21 | 1.69 | 90 |
| F2-5 C. | Clear | 98.34 | 0.78 | 0.88 | 90 |
| F2-25 C. | Clear | 97.42 | 1.20 | 1.38 | 90 |
| F2-37 C. | Clear | 94.63 | 3.06 | 2.31 | 85 |
| T = 12 Weeks | | | | | |
| F1-5 C. | Clear | 98.25 | 0.73 | 1.02 | 98 |
| F1-25 C. | Clear | 97.07 | 1.26 | 1.62 | 90 |
| F1-37 C. | Clear | 93.31 | 3.88 | 2.81 | 84 |
| F2-5 C. | Clear | 98.30 | 0.70 | 1.00 | 94 |
| F2-25 C. | Clear | 97.22 | 1.30 | 1.48 | 88 |
| F2-37 C. | Clear | 92.88 | 4.05 | 1.54 | 82 |

Example 5

Stability Data of Two Daclizumab Formulations in Histidine Buffer

Formulations 3 and 4 are prepared according to Example 3.

Formulation 3: 100 mg/ml Daclizumab antibody, 50 mM histidine (pH 6.0), 115 mM NaCl, 0.03% Tween®-80, purged with nitrogen.

Formulation 4: same as Formulation 3, plus 0.05% EDTA.

The stability results of Formulations 3 and 4 at T=0, 2 weeks, 4 weeks, 8 weeks, and 12 weeks are shown as follows at 5, 25, and 37° C. (Table 6).

TABLE 6

Stability results of Formulations 3 and 4.

| Sample | Clarity | % Monomer | % Clip | % Aggregate | % Potency |
|---|---|---|---|---|---|
| T = 0 | | | | | |
| F3 | Clear | 99.24 | 0.43 | 0.33 | 79 |
| F4 | Clear | 99.01 | 0.68 | 0.32 | 89 |
| T = 2 Weeks | | | | | |
| F3-5 C. | Clear | 99.24 | 0.38 | 0.38 | ND |
| F3-25 C. | Clear | 99.09 | 0.47 | 0.44 | ND |
| F3-37 C. | Clear | 98.32 | 1.01 | 0.67 | ND |
| F4-5 C. | Clear | 99.19 | 0.44 | 0.37 | ND |
| F4-25 C. | Clear | 99.11 | 0.47 | 0.42 | ND |
| F4-37 C. | Clear | 98.41 | 0.93 | 0.66 | ND |
| T = 4 Weeks | | | | | |
| F3-5 C. | Clear | 99.26 | 0.37 | 0.35 | 91 |
| F3-25 C. | Clear | 98.99 | 0.56 | 0.45 | 76 |
| F3-37 C. | Clear | 97.96 | 1.42 | 0.62 | 83 |
| F4-5 C. | Clear | 99.28 | 0.38 | 0.34 | 81 |
| F4-25 C. | Clear | 99.00 | 0.56 | 0.44 | 85 |
| F4-37 C. | Clear | 97.94 | 1.44 | 0.63 | 79 |
| T = 8 Weeks pH 6.0 | | | | | |
| F3-5 C. | Clear | 99.24 | 0.38 | 0.38 | 86 |
| F3-25 C. | Clear | 98.74 | 0.72 | 0.54 | 82 |
| F3-37 C. | Clear | 96.87 | 2.37 | 0.76 | 75 |
| F4-5 C. | Clear | 99.23 | 0.39 | 0.38 | 97 |
| F4-25 C. | Clear | 98.71 | 0.75 | 0.54 | 92 |
| F4-37 C. | Clear | 96.90 | 2.34 | 0.76 | 86 |
| T = 12 Weeks pH 6.0 | | | | | |
| F3-5 C. | Clear | 98.89 | 0.63 | 0.49 | 99 |
| F3-25 C. | Clear | 98.04 | 1.21 | 0.75 | 96 |
| F3-37 C. | Clear | 94.79 | 4.06 | 1.17 | 90 |
| F4-5 C. | Clear | 98.92 | 0.60 | 0.48 | 91 |
| F4-25 C. | Clear | 98.06 | 1.23 | 0.72 | 87 |
| F4-37 C. | Clear | 95.02 | 3.83 | 1.15 | 78 |

Example 6

Stability Data of Daclizumab Formulation at Room Temperature for One Year

A liquid antibody formulation of 100 mg/ml Daclizumab in 30 mM sodium succinate, pH 6, 100 mM NaCl, and 0.03% Tween® 80 was tested for stability after one year storage at 25° C. The stability results indicate that the formulation is stable for at least one year at 25° C. (Table 7).

TABLE 7

Stability Results of Daclizumab formulation after One-Year Storage at 25° C.

| Sample | Clarity | % Monomer | % Clip | % Aggregate | % Potency |
|---|---|---|---|---|---|
| T = 0 | Clear | 98.27 | 0.77 | 0.96 | 100 |
| T = 1 year | Clear | 94.32 | 3.14 | 2.53 | 86 |

Example 7

Stability Data of Daclizumab Formulation at 5° C. for 18 Months

A liquid antibody formulation of 100 mg/ml Daclizumab in 30 mM sodium succinate, pH 6, 100 mM NaCl, and 0.03% Tween® 80 was incubated at 5° C. (2-8° C.) and tested for stability at different time points. The stability results indicate that the formulation is stable for at least 18 months at refrigerated temperature (Table 8).

TABLE 8

Stability Results of Daclizumab at 5° C.

| Time (Month) | % Monomer | % Aggregate |
|---|---|---|
| 0 | 99.0 | N/A |
| 3 | 99.1 | 0.2% |
| 6 | 99.1 | 0.2% |
| 9 | 98.8 | 0.2% |
| 12 | 98.9 | 0.2% |
| 18 | 98.6 | 0.2% |

Example 8

Stability Data of HAIL-12 (Histidine Buffer)

HAIL-12 (anti-IL12 antibody, 50 mg/mL) was formulated in 50 mM Histidine buffer, 120 mM sodium chloride, 0.03% Tween 80, pH 6.0. The on-going stability testing indicates that the formulation is stable at 5° C. for at least 9 months (Table 9).

TABLE 9

Stability Results of HAIL-12 at 5° C.

| Sample | Clarity | % Monomer | % Clip | % Aggregate | % Potency |
|---|---|---|---|---|---|
| T = 0 | Clear | 99.47 | 0.18 | 0.35 | 95 |
| T = 7 months | Clear | 98.90 | 0.65 | 0.45 | — |
| T = 8 months | — | — | — | — | 100 |
| T = 9 months | — | 98.52 | — | — | — |

Example 9

Stability Data of HAIL-12 (Succinate Buffer)

HAIL-12 (50 and 100 mg/mL) was formulated in 40 mM Na-succinate buffer, 100 mM NaCl, and 0.03% Tween-80, pH 6.0. The ongoing stability testing indicates that the formulation is stable at 5, 25, and 37° C. for at least 12 weeks (Tables 10 and 11).

TABLE 10

Stability Results of HAIL-12 (50 mg/mL) at various temperatures.

| Sample | Clarity | % Monomer | % Clip | % Aggregate | % Potency |
|---|---|---|---|---|---|
| T = 0 | | | | | |
| 5° C. | Clear | 99.27 | 0.27 | 0.47 | 99 |
| T = 12 Weeks | | | | | |
| 5° C. | Clear | 99.00 | 0.34 | 0.67 | 109 |
| 25° C. | Clear | 98.05 | 0.92 | 1.04 | 76 |
| 37° C. | Clear | 93.86 | 4.25 | 1.90 | 75 |
| T = 6 Months | | | | | |
| 5° C. | Clear | 98.63 | 0.61 | 0.76 | 97 |
| 25° C. | Clear | 97.1 | 1.67 | 1.22 | 78 |

TABLE 11

Stability Results of HAIL-12 (100 mg/ml) at various temperatures.

| Sample | Clarity | % Monomer | % Clip | % Aggregate |
|---|---|---|---|---|
| T = 0 | | | | |
| 5° C. | Clear | 99.2 | 0.31 | 0.49 |
| T = 12 Weeks | | | | |
| 5° C. | Clear | 98.9 | 0.31 | 0.78 |
| 25° C. | Clear | 97.67 | 0.95 | 1.38 |
| 37° C. | Clear | 93.26 | 4.14 | 2.6 |

Example 11

Stability Data of HuEP5C7

HuEP5C7 (anti-L selectin antibody, 50 and 100 mg/mL) was formulated in 50 mM histidine buffer, 125 mM sodium chloride, 0.01% Tween 80, pH 6.0. The on-going stability testing indicates that the formulation is stable for three months at 25° C. and 45° C. and for at least 9 months at 5° C. The results of the 9-month stability testing at 5° C. is shown in Table 12. The results of the 3-month accelerated stability testing is shown in Table 13.

TABLE 12

Stability Results of HuEP5C7 at 5° C.

| Sample | % Monomer | % Clip | % Aggregate | % Potency |
|---|---|---|---|---|
| 50 mg/mL | | | | |
| T = 0 | 98.54 | 0.30 | 1.17 | 83 |
| T = 9 months | 99.08 | 0 | 0.91 | 99 |
| 100 mg/mL | | | | |
| T = 0 | 98.56 | 0.23 | 1.21 | 79 |
| T = 9 months | 98.05 | 0.03 | 1.47 | 90 |

TABLE 13

Stability Results of HuEP5C7 at various temperatures.
T = 3 months

| Sample | % Monomer | % Clip | % Aggregate | % Potency |
|---|---|---|---|---|
| 50 mg/mL - 5° C. | 99.48 | 0.14 | 0.39 | 121 |
| 50 mg/mL - 25° C. | 98.81 | 0.31 | 0.88 | 72 |
| 50 mg/mL - 45° C. | 98.26 | 0.99 | 0.76 | 107 |
| 100 mg/mL - 5° C. | 99.03 | 0 | 0.97 | 93 |
| 100 mg/mL - 25° C. | 98.56 | 0.40 | 1.06 | 78 |
| 100 mg/mL - 45° C. | 97.88 | 0.92 | 1.20 | 91 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A stable aqueous pharmaceutical formulation, comprising:
   about 20 mM to about 60 mM succinate buffer,
   about 0.01% to about 0.1% polysorbate,
   about 75 mM to about 150 mM sodium chloride, and
   at least about 100 mg/ml of a daclizumab antibody,
   wherein said aqueous pharmaceutical formulation has a pH in the range of about pH 5.5 to about pH 6.5; and
   wherein the daclizumab in said aqueous pharmaceutical formulation shows no more than 10% aggregation after 3 months at room temperature as measured by size exclusion chromatography.

2. The stable aqueous pharmaceutical formulation of claim 1 in which the polysorbate is polysorbate 80.

3. The stable aqueous pharmaceutical formulation of claim 1 in which the succinate buffer is sodium succinate.

4. The stable aqueous pharmaceutical formulation of claim 1 which has a pH of about pH 6.0.

5. The stable aqueous pharmaceutical of claim 1, in which the amount of polysorbate is about 0.01% to about 0.05%.

6. The stable aqueous pharmaceutical of claim 1, in which the amount of polysorbate is about 0.02% to about 0.04%.

7. The stable aqueous pharmaceutical formulation of claim 1, wherein the daclizumab in said aqueous pharmaceutical formulation shows no more than 5% aggregation after 3 months at room temperature as measured by size exclusion chromatography.

8. The stable aqueous pharmaceutical formulation of claim 1, wherein the daclizumab in said aqueous pharmaceutical formulation shows no more than 10% aggregation after 6 months at room temperature as measured by size exclusion chromatography.

9. The stable aqueous pharmaceutical formulation of claim 1, wherein the daclizumab in said aqueous pharmaceutical formulation shows no more than 5% aggregation after 6 months at room temperature as measured by size exclusion chromatography.

* * * * *